United States Patent [19]

Dockner et al.

[11] Patent Number: 4,599,202

[45] Date of Patent: Jul. 8, 1986

[54] PREPARATION OF ADIPODINITRILE

[75] Inventors: Toni Dockner, Meckenheim; Manfred Sauerwald, Roedersheim-Gronau; Jost H. Manegold, Lambsheim; Hans Leitner, Flomersheim, all of Fed. Rep. of Germany

[73] Assignee: BASF Aktiengesellschaft, Fed. Rep. of Germany

[21] Appl. No.: 751,390

[22] Filed: Jul. 3, 1985

[30] Foreign Application Priority Data

Jul. 5, 1984 [DE] Fed. Rep. of Germany ....... 3424701

[51] Int. Cl.$^4$ .......................................... C07C 120/08
[52] U.S. Cl. ................................................. 558/313
[58] Field of Search ..................................... 260/465.2

[56] References Cited

U.S. PATENT DOCUMENTS

| | | | |
|---|---|---|---|
| 3,153,084 | 10/1964 | Veazey et al. | 260/465.2 |
| 3,299,116 | 1/1967 | Romani et al. | 260/465.2 |
| 3,459,783 | 8/1969 | Budnick | 260/465.2 |
| 3,629,316 | 12/1971 | Hatten et al. | 260/465.2 |
| 3,850,974 | 11/1974 | Lichtenwalter et al. | 260/465.2 X |

FOREIGN PATENT DOCUMENTS 537954  7/1941  United Kingdom .

*Primary Examiner*—Joseph Paul Brust
*Attorney, Agent, or Firm*—Keil & Weinkauf

[57] ABSTRACT

Adipodinitrile is prepared by reacting adipic acid with excess ammonia at from 250° to 350° C. in the liquid phase in the presence of a diluent by a process in which a liquid hydrocarbon which is inert under the reaction conditions is used as the diluent.

8 Claims, No Drawings

PREPARATION OF ADIPODINITRILE

Adipodinitrile is prepared industrially on a large scale by reacting adipic acid with ammonia. In a process described in U.S. Pat. No. 3,153,084, adipic acid and ammonia are reacted in the gas phase over a sintered boric acid/phosphoric acid catalyst to give adipodinitrile. However, the gas-phase method has the disadvantage that the catalyst is rapidly deactivated as a result of becoming coated with decomposition products, and furthermore substantial amounts of by-products which are difficult to separate off, such as 2-cyanocyclopenten-1-ylamine and 1-cyanocyclopentanone, are formed. In another process, described in British Pat. No. 537,954, molten adipic acid is reacted with ammonia in the presence of an acidic catalyst, such as phosphoric acid. However, this process gives adipodinitrile only in moderate yields. Furthermore, U.S. Pat. No. 3,299,116 discloses a process for the preparation of adipodinitrile in which adipic acid, dissolved in adipodinitrile as a diluent, is reacted with ammonia in the presence of an acidic catalyst, such as phosphoric acid. However, this process has the disadvantage that the adipodinitrile used as diluent has to be circulated in relatively large amounts. In this procedure, the adipodinitrile has to be separated off from the catalyst and from the crack products, and recycled. Moreover, adipodinitrile is repeatedly subjected to harmful high temperature, with the result that undesirable by-products are formed.

It is an object of the present invention to prepare adipodinitrile by reacting adipic acid with ammonia in the liquid phase by a method in which adipodinitrile is exposed to the harmful high reaction temperatures for only a short time, the catalyst may not be separated off continuously, the formation of undesirable by-products is reduced, and the crack products are separated off from the desired products and remain in the diluent.

We have found that this object is achieved by a process for the preparation of adipodinitrile by reacting adipic acid with excess ammonia at from 250° to 350° C. in the liquid phase in the presence of a diluent, wherein the reaction is carried out in the presence of, as a diluent, a liquid hydrocarbon which is inert under the reaction conditions.

The advantages of the novel process are that large amounts of diluents do not have to be circulated, adipodinitrile is exposed to the high reaction temperatures for only a short time, any catalysts used can remain in the diluent, and finally fewer undesirable by-products are formed and the purification of the adipodinitrile is simplified because the crack products remain in the diluent.

According to the invention, the starting material used is adipic acid, which is advantageously fed to the reaction in molten form, for example at from 160° to 180° C. Adipic acid is reacted with excess ammonia, advantageously in an amount of from 3 to 15, in particular from 5 to 10, moles per mole of adipic acid.

According to the invention, the reaction is carried out in a liquid hydrocarbon which is inert under the reaction conditions, high-boiling mineral oil fractions preferably being used. Examples of suitable diluents are vacuum gas oil, vacuum residues, heavy fuel oil, molten paraffin wax and aromatic hydrocarbon oil. Advantageously, the diluent has a boiling point of not less than 350° C., in particular from 400° to 550° C.

The reaction is carried out at from 250° to 350° C., in particular from 280° to 330° C., in general under atmospheric pressure. However, it is also possible to carry out the reaction under slightly superatmospheric pressure or reduced pressure.

The reaction is advantageously effected in the presence of a catalyst, examples of suitable catalysts being phosphoric acid, phosphoric acid on a carrier, such as silica, phosphates, preferably high-boiling phosphates, in particular high-boiling monoesters of phosphoric acid, such as mono-p-nonylphenyl phosphate, and ammonium salts of phosphoric acid, such as mono-(N-methylditridecylammonium) dihydrogen phosphate. Insoluble catalysts are advantageously used in suspension in the diluent. The catalysts are advantageously added to the diluent in an amount of from 0.01 to 25, preferably from 0.1 to 10, in particular from 0.5 to 5, % by weight.

Sparingly volatile by-products, such as polymers and tar-like decomposition products remain in suspended or dissolved form in the diluent and can be removed together with this by a continuous or batchwise procedure. It is therefore advantageous to replace some of the diluent, for example from 0.1 to 10% by weight per hour. The mineral oil separated off is advantageously burned to generate energy. The amounts of diluent and, where relevant, catalyst which have been separated off are of course replaced. Adipodinitrile is preferably discharged from the reaction mixture at the rate at which it is formed, as a rule together with intermediates.

For example, adipodinitrile, intermediates, such as cyanovaleric acid and cyanovaleramide, water, carbon dioxide and volatile by-products are discharged from the liquid reaction mixture, together with the excess ammonia. The gaseous product discharged is advantageously cooled and fed to a distillation column. Ammonia, water and small amounts of carbon dioxide, cyclopentanone and cyclopentanone derivatives are taken off via the top. Ammonia is separated off and recycled to the reaction. Technical grade adipodinitrile is obtained as a middle fraction. Intermediates, such as cyanovaleric acid and cyanovaleramide, remain at the bottom of the column and are likewise recycled to the reaction.

The reaction is carried out in, for example, stirred kettles, cylindrical reactors or packed columns. These are advantageously charged, for example to as much as ⅔, with the inert hydrocarbon which is used as a diluent and may contain a catalyst. Molten adipic acid and gaseous ammonia are advantageously fed in continuously from below, the amount of adipic acid introduced preferably being from 0.1 to 2 kg per liter of reaction volume (diluent) per hour. The liquid reaction mixture is kept at the abovementioned temperature, and the products discharged with the excess ammonia are condensed and then separated by distillation. Some of the inert hydrocarbon containing by-products is taken off continuously and replaced with fresh inert hydrocarbon.

The Examples which follow illustrate the process according to the invention.

EXAMPLE 1

A stirred kettle having a capacity of 2 l is charged with 1,000 g of vacuum residues (bp. 400° C.) containing 1% by weight of phosphoric acid. The vacuum residues are kept at 300° C., and 100 g/hour of molten adipic acid (160° C.) and 150 l (S.T.P.)/hour of ammonia are fed in from below. The gaseous products leaving the stirred kettle are cooled and distilled, and excess ammonia is recycled. After a reaction time of 5 hours, 225.1 g of technical grade adipodinitrile and 150 g of a residue essentially consisting of intermediates are obtained. The latter are recycled to the reaction, a further 114.7 g of adipodinitrile being obtained. This corresponds to a total yield of 91.8%.

EXAMPLE 2

The procedure described in Example 1 is followed, except that 10% by weight of a catalyst comprising 10% by weight of phosphoric acid on silica is used. 300 g/hour of molten adipic acid and 370 l (S.T.P.)/hour of ammonia are fed in. The remaining reaction conditions correspond to those of Example 1. After a reaction time of 5 hours, 723.7 g of technical grade adipodinitrile are obtained. 310 g of a distillation residue which essentially consists of intermediates are recycled to the reaction, and a further 229.6 g of adipodinitrile are obtained. This corresponds to a total yield of 85.9%.

EXAMPLE 3

A heatable tube having an internal diameter of 60 mm and a length of 1500 m is charged with 1,000 g of vacuum residues and heated at 300° C. 100 g/hour of molten adipic acid and 150 l (S.T.P.)/hour of ammonia are fed in from below, and the gaseous by-products are taken off at the top of the tube, condensed and separated. Excess ammonia is recycled to the reaction. After a reaction time of 5 hours, with recycling of the resulting intermediates, a total of 251.6 g of technical grade adipodinitrile are obtained. The yield is 68.0%.

EXAMPLE 4

The reactor described in Example 3 is charged with 1,700 g of vacuum residues which contain 1% by weight of phosphoric acid. 1,000 g/hour of molten adipic acid and 1,500 l (S.T.P.)/hour of ammonia are passed in from below at 300° C., and the gaseous reaction mixture leaving the reactor is cooled and distilled. Excess ammonia and the distillation residue, which consists of intermediates, are recycled. 705 g/hour of adipodinitrile are obtained as a middle fraction. This corresponds to a yield of 95.3%. Furthermore, 50 g/hour of the reactor content are discharged, and replaced with fresh catalyst-containing vacuum residues.

We claim:

1. A process for the preparation of adipodinitrile which comprises reacting adipic acid with excess ammonia at from 250° to 350° C. in the liquid phase in the presence of, as a diluent, a liquid hydrocarbon having a boiling point of from 350° to 550° C., which is inert under the reaction conditions.

2. A process as defined in claim 1, wherein from 3 to 15 moles of ammonia are used per mole of adipic acid.

3. A process as defined in claim 1, wherein excess ammonia is recycled.

4. A process as defined in claim 1, wherein phosphoric acid, a phosphate or an ammonium salt of phosphoric acid is concomitantly used as a catalyst.

5. A process as defined in claim 1, wherein adipic acid is introduced in an amount of from 0.1 to 2 kg per hour, per liter of reaction space.

6. A process as defined in claim 1, wherein the rate of discharge of adipodinitrile from the reaction mixture is equal to the rate of formation of adipodinitrile.

7. A process as defined in claim 1, wherein some of the diluent containing sparingly volatile by-products is removed, and replaced with fresh diluent.

8. A process as defined in claim 1, wherein the liquid hydrocarbon selected from the group consisting of vacuum gas oil, vacuum residues, heavy fuel oil, molten paraffin wax and aromatic hydrocarbon oil.

* * * * *